(12) United States Patent
Liu et al.

(10) Patent No.: US 12,002,551 B2
(45) Date of Patent: Jun. 4, 2024

(54) METHOD TO DISTINGUISH PEROXISOME PROLIFERATOR-ACTIVATED RECEPTOR GAMMA FULL AGONIST, PARTIAL AGONIST AND ANTAGONIST WITH DIFFERENT ACTIVITIES AND IDENTIFICATION THEREOF

(71) Applicant: Nanjing University, Nanjing (CN)

(72) Inventors: Hongling Liu, Nanjing (CN); Laihao Shi, Nanjing (CN)

(73) Assignee: Nanjing University, Nanjing (CN)

( * ) Notice: Subject to any disclaimer, the term of this patent is extended or adjusted under 35 U.S.C. 154(b) by 1052 days.

(21) Appl. No.: 16/816,306

(22) Filed: Mar. 12, 2020

(65) Prior Publication Data

US 2020/0372978 A1 Nov. 26, 2020

(30) Foreign Application Priority Data

May 21, 2019 (CN) .......................... 201910425983.6

(51) Int. Cl.
| | |
|---|---|
| G16C 20/50 | (2019.01) |
| C07K 1/04 | (2006.01) |
| C07K 14/705 | (2006.01) |
| G16B 5/00 | (2019.01) |
| G16B 15/00 | (2019.01) |
| G16C 20/70 | (2019.01) |

(52) U.S. Cl.
CPC ................ *G16C 20/50* (2019.02); *C07K 1/04* (2013.01); *C07K 14/70567* (2013.01); *G16B 5/00* (2019.02); *G16B 15/00* (2019.02); *G16C 20/70* (2019.02)

(58) Field of Classification Search
None
See application file for complete search history.

(56) References Cited

PUBLICATIONS

Ohashi et al. "Different structures of the two peroxisome proliferator-activated receptor gamma (PPARγ) ligand-binding domains in homodimeric complex with partial agonist, but not full agonist." Bioorganic & Medicinal Chemistry Letters. 2015. vol. 25, pp. 2639-2644. (Year: 2015).*
Fratev 2016. "PPARγ helix 12 exhibits an antagonist conformation." Physical Chemistry Chemical Physics. vol. 18, pp. 9272-9280. (Year: 2016).*
Fratev 2017. "PPARγ non-covalent antagonists exhibit mutable binding modes with a similar free energy of binding: A case study." Journal of Molecular Biology. vol. 35(3), pp. 476-485. (Year: 2017).*
Fratev et al. "Structural and Dynamical Insight into PPARγ Antagonism: In Silico Study of the Ligand-Receptor Interactions of Non-Covalent Antagonists." International Journal of Molecular Sciences. 2015. vol. 16, pp. 15405-15424. (Year: 2015).*
Xu et al. "Molecular Modeling of the 3D Structure of 5-HT1AR: Discovery of Novel 5-HT1AR Agonists via Dynamic Pharmacophore-Based Virtual Screening." Journal of Chemical Information and Modeling. 2013. vol. 53, pp. 3202-3211. (Year: 2013).*
Li et al. "3D-QSAR and Molecular Docking Studies on Benzotriazoles as Antiproliferative Agents and Histone Deacetylase Inhibitors." Bulletin of the Korean Chemical Society. 2013. vol. 34(8), pp. 2387-2393. (Year: 2013).*
Vogele et al. "Molecular dynamics simulations of carbon nanotube porins in lipid bilayers." Faraday Discussions. 2018. vol. 209, pp. 341-358. (Year: 2018).*
Graen et al. "Amber-Dyes: Characterization of Charge Fluctuations and Force Field Parameterizations of Fluorescent Dyes for Molecular Dynamics Simulations." Journal of Chemical Theory and Computation. 2014. vol. 10, pp. 5505-5512. (Year: 2014).*
Nash et al. "Mapping intermolecular interactions and active site conformations: from human MMP-1 crystal structure to molecular dynamics free energy calculations." Journal of Biomolecular Structure and Dynamics. 2017. vol. 35(3), pp. 564-573. (Year: 2017).*
Barrozo et al. "Computer simulations of the catalytic mechanism of wild-type and mutant B-phophoglucomutase." Organic & Biomolecular Chemistry. 2018. vol. 16, pp. 2060-2073. (Year: 2018).*
Bizzarri et al. "MD simulation of a plastocyanin mutant adsorbed onto a gold surface." Biophysical Chemistry. 2003. vol. 106, pp. 111-123. (Year: 2003).*
Khan et al. "Allosteric ligands for the pharmacologically important Flavivirus target (NS5) from Zinc database based on pharmacophoric points, free energy calculations and dynamics correlation." Journal of Molecular Graphics and Modeling. 2018. vol. 82, pp. 37-47. (Year: 2018).*
Fang et al. "Activation of Human Peroxisome Proliferator-Activated Nuclear Receptors (PPARγ1) by Semi-Volatile Compounds (SVOCs) and Chemical Mixtures in Indoor Dust." Environmental Science & Technology. 2015. vol. 49, pp. 10057-10064. (Year: 2015).*
Fratev et al. "Prediction of Accurate Binding Modes Using Combination of Classical and Accelerated Molecular Dynamics and Free-Energy Perturbation Calculations: An Application to Toxicity Studies." ACS Omega, vol. 3, pp. 4357-4371. (Year: 2018).*

\* cited by examiner

*Primary Examiner* — John S Brusca
*Assistant Examiner* — Steven W. Bailey
(74) *Attorney, Agent, or Firm* — Idea Intellectual Limited; Margaret A. Burke; Sam T. Yip

(57) ABSTRACT

The present invention discloses a method of constructing a pharmacophore to determine whether a molecule is a peroxisome proliferator-activated receptor γ full agonist, partial agonist or antagonist in terms of a binding energy or a free energy surface comprising: providing a protein receptor mimicking said peroxisome proliferator-activated receptor γ and a corresponding ligand; docking the corresponding ligand and the protein receptor to form a docked conformation; performing at least two rounds of molecular dynamic simulation to obtain at least one trajectory and at least one free energy surface; inputting the trajectory to construct at least one pharmacophore and obtaining the binding energy of the corresponding ligand; comparing the molecule with the corresponding ligand in terms of the binding energy thereof to the protein receptor in order to determine whether the molecule is the peroxisome proliferator-activated receptor γ full agonist, partial agonist or antagonist.

3 Claims, 21 Drawing Sheets

METHOD TO DISTINGUISH PEROXISOME PROLIFERATOR-ACTIVATED RECEPTOR GAMMA FULL AGONIST, PARTIAL AGONIST AND ANTAGONIST WITH DIFFERENT ACTIVITIES AND IDENTIFICATION THEREOF

CROSS-REFERENCE TO RELATED APPLICATION

This application claims priority from the Chinese Patent Application Number 2019104259836 filed on May 21, 2019, and the disclosure of which is incorporated herein by reference in its entirety.

FIELD OF THE INVENTION

The present invention relates to the technical field of endocrine disrupting chemicals recognition. More particularly, it relates to a method of constructing a pharmacophore to determine whether a molecule is a peroxisome proliferator-activated receptor γ full agonist, partial agonist or antagonist in terms of a binding energy or a free energy surface thereof.

BACKGROUND

Endocrine disrupting chemicals (EDCs) only need trace amount to produce significant adverse effects, therefore it has attracted people's attention. The endocrine disrupting effects mediated by the nuclear receptors can be divided into two types: agonist effect and antagonistic effect. Up to now, more than 142 million chemicals have been synthesized and registered by human beings, and the number is still rising, among which a large number of substances with potential endocrine disrupting effects need to be identified. However, the existing in vivo and in vitro experimental techniques are unable to deal with the increasing number of compounds to be screened.

The conventional quantitative structure-activity relationship (QSAR) can only predict the activity of the compound while it is known as a nuclear receptor agonist/antagonist, however it cannot distinguish whether an unknown compound belongs to a full agonist, partial agonist or antagonist, and the prediction method is generally applied to a class of compounds with similar structure. When the number of compounds increases, the prediction efficiency will be significantly declined.

PPARγ has not only a repressive and a mimicry state, but also a partial activated state between them. Therefore, the ligands of PPARγ can be divided into full agonists, partial agonists and antagonists. The existing studies on the structural analysis of PPARγ indicate that when PPARγ is combined with full agonists, two PPARγ in the PPARγ dimers are all activated, when PPARγ is combined with partial agonists, one of the two PPARγ in the PPARγ dimer is in an activated state and the other is in a non-activated state.

However, the antagonistic conformation of PPARγ has not been resolved yet. Most of the existing studies use the known PPARγ activity, and then perform the simulation of the activated state of PPARγ to identify the substances activity. Due to the limitation of the sampling efficiency of the conventional molecular dynamics technology, the simulation of tens or even hundreds of nanosecond (ns) are not enough to find the real stable structure, which makes it difficult to distinguish the activity of PPARγ interference substances only by using the conventional molecular dynamics technology.

Molecular dynamic simulation (MD), the conventional MD (cMD) technology is difficult to cross the higher free energy barrier under the limited simulation time, which leads to a problem of low sampling efficiency, and most of the research only focuses on a certain kind of compounds with similar structure. The conventional MD technology is not able to distinguish the interfering substance activity of the PPARγ full agonist, partial agonist and antagonist.

SUMMARY OF THE INVENTION

This section aims to summarize some aspects of the embodiments of the present invention and to briefly describe some preferred embodiments. The simplification or omission may be made in this section, the abstract of the specification, and the title to avoid obscuring the purpose of this section, the abstract of the specification, and the title. Such simplification or omission may not be used to limit the scope of the present invention.

The present invention has been made in view of the above-mentioned technical drawbacks and provides a method of constructing a pharmacophore to determine whether a molecule is a peroxisome proliferator-activated receptor γ full agonist, partial agonist or antagonist in terms of a binding energy or a free energy surface thereof The benefit of the present invention: Firstly, the molecular dynamics simulation is used to simulate the conformational changes of PPARγ after binding to the full agonists, antagonists and partial agonists. It is found that the full agonists and partial agonists are still difficult to distinguish, which shows that the molecular dynamics simulation is limited by the sampling efficiency and cannot obtain all the low energy conformations of PPARγ after binding to the partial agonists. However, after using the Well-Tempered Meta-dynamic molecular dynamic simulation, the present invention has obtained the free energy surface of full agonists, partial agonists and antagonists after binding with PPARγ. The present invention can qualitatively distinguish PPARγ activity by using free energy surface, wherein the agonist conformations only exist when the PPARγ binds with the agonists, and the agonist and antagonistic conformations co-exist when PPARγ binds with the partial agonists. The present invention can quickly distinguish the PPARγ activity of compounds with different structures and greatly reduce the use of chemicals and cells in the laboratory in the process of traditional toxicological experiment, the workload of the laboratory and save the expenses of the laboratory; Therefore, PPARγ activity of compounds is identified before QSAR modeling, which makes the results of QSAR modeling close to the reality, such that the conventional QSAR can be widely used.

BRIEF DESCRIPTION OF THE DRAWINGS

FIG. 2A to FIG. 2Z are the free energy surfaces of the full agonists, the partial agonists and the antagonists obtained by the WT-metadynamic simulation; wherein FIG. 2A to FIG. 2E show the free energy surface of PPARγ after binding to the agonists; FIG. 2G to FIG. 2Z show the free energy surface of PPARγ after binding to the partial agonists.

FIG. 3A to FIG. 3C are the PPARγ conformation, wherein FIG. 3A shows the corresponding conformation of the PPARγ H12 binding to the full agonist ROSI of the free energy surface and the conformation of holo-PPARγ; FIG. 3B shows the corresponding conformation of PPARγ binding to the antagonist 9P and the antagonist conformation of PPARα; FIG. 3C shows the corresponding conformation of PPARγ binding to the partial agonist DiBP and the antagonist conformation of PPARα.

FIG. 4A is shown as agonist; FIG. 4B is shown as partial agonist.

DETAILED DESCRIPTION

Embodiment 1

Materials and Data Collection

The substances used in the present invention are from the dust in the background room by Mingliang Fang et al in 2015. The researchers analysed a variety of substances from indoor dust in Beijing, including a variety of flame retardants and their metabolites. According to the previous activation and binding experiments of PPARγ, it has been shown that most of these substances are full or partial agonists to PPARγ. The researchers used rosiglitazone and PPAR endogenous ligand 15d-PJG2 as positive controls and reporter gene assay to study the PPARγ activity of these substances. The activity data in the present invention were from this research. Before using the data, the EC15 of each substance is first converted to the equivalent of rosiglitazone, and then the logarithm is taken.

Receptor and Ligand Modeling

Figure 1:
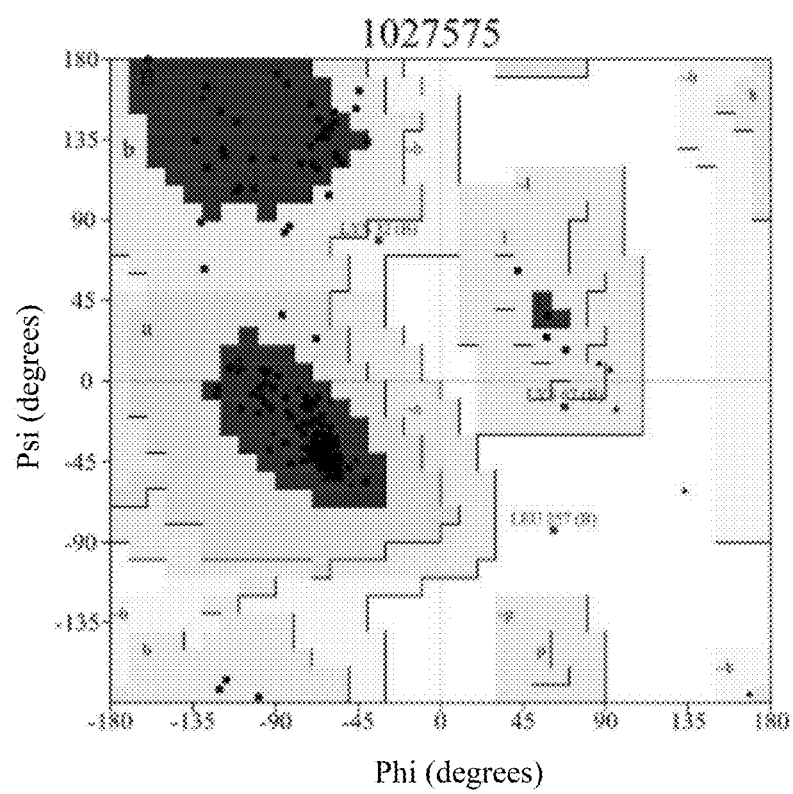
FIG. 1 is the Ramachandran plot of the modeling protein structure.

The template for the molecular protein structure of PPARγ (PDB ID: 3VSO) is from the RCSB protein data bank. Before docking, remove the small molecules mekt21 in the A chain and B chain, all the water molecules to obtain the remaining B chain protein, then the remaining B chain protein is used as the template for the homology modeling in the next step. The receptor sequence for homology modeling is from Uniprot (Uniprot ID: P37231), then the homology modeling is performed on the Swiss-model platform, and the modeling protein structure is verified by Ramachandran plot (see FIG. 1). The results show 92.1% of all the amino acid residues are in the favored region, 6.6% are in the allowed region, and 0.8% are in generously allowed region, which means the constructed PPARγ structure in the present invention is reasonable. All ligand small molecules are constructed by Sketch Molecule module in sybyl7.3 (Tripos Inc., St. Louis, MO, USA) and optimize the structure with Minimize module in sybyl7.3. The process is as follows: Use Powell method to optimize, give Gasteiger-Hückel charge, use standard Tripos molecular force field, perform energy optimization, the standard restrained energy is 0.001 kcal/(mol Å), and the maximum number of iterations are 1000 times.

Molecules Docking

Surflex-Dock module in sybyl7.3 is used to dock the ligand small molecules to the receptor protein. When docking, use the Automatic mode to search the binding pocket with the threshold value is 0.5, and the bloat value is 0. The flexibility of the ring is also considered during the docking, and each compound generates 20 binding conformations. The highest scoring conformation is the most likely bioactive conformation for the molecular dynamic simulation in the next step.

Molecular Dynamic Simulation

Gromacs-5.14 is used to perform MD simulation. During the simulation process, the Amber GAFF force field is used for the ligand small molecules and the small molecules in the receptors. The process is as follows: Gaussian09 D01 is firstly used to optimize the structure of small molecules, calculates the electrostatic potential, fit the RESP charge, then use the Antechamber module in Ambertools to generate RESP file, and use the acpype.py script to generate Gromacs available molecular topology file. The protein topological file is generated by pdb2gmx, and Amber99sb.ff is used as force field. The box is constructed at least 2 nm away from the surface of proteins—ligand small molecules, and then TIP3P water molecules is filled in, i.e. there is at least 2 nm at the margin of protein from solvent, and sodium ion is added to neutralize the charge in the system.

Before performing dynamic simulation, the system undergoes 5000 steps of energy minimization. The system is then equilibrated by following two stages: Canonical ensemble (NVT) and Isothermal-isobaric (NPT) ensemble. Each system is simulated as 500 ps in the NVT ensemble, heating gradually from 0 to 300K under minimum energy, and equilibrating under 500 ps at 300K in the NPT ensemble. Finally, the MD simulation is carried out under 20 ns and recorded the trajectory every 2 ps.

Well-Tempered Meta-Dynamic Molecular Dynamic Simulation

Under regular temperature and pressure, protein molecules with nanosecond(ns) level from MD simulation are often limited to a local potential energy well. In order to achieve ideal results, it is preferred to select Well-Tempered Meta-dynamic simulation method in the present invention to deal with the sampling efficiency problem in the molecular dynamics simulation by adding artificial Gaussian bias potential to the energy of manually selected collective variable (CV) to accelerate the motions of the system along these variabilities, resulting in jumping out of the local potential well and obtain the overall free energy surface.

Gromacs-5.1.4 patched by Pumed2 is used to perform Well-Tempered Meta-dynamic simulation, the force field and other simulation parameters are the same as unbiased sampling, and the selection of collective variable (CV) is an important step in the process of meta-dynamic simulation. In this simulation, CV1 is the distance between the Cα of Tyr473 on helix 12 (H12) to Cα of Leu453 on helix 11 (H11), and CV2 is the distance between Cα of Tyr473 on H12 to Cα of Lys319 on H4. The rest of the other parameters are as follows: Gaussian width 0.4 kcal/mol, Gaussian width ω 0.025 nm, interval 2ps, and each substance simulation lasts for 80 ns. At the end of the simulation, the energy deviation of CV is used to check whether the simulation converges.

Pharmacophore Construction

After competing molecular dynamics simulation and identifying full agonists and partial full agonists according to the free energy surface, the pharmacophore is further analyzed and predicted quantitatively. First of all, the activated conformation of binding full agonist (for example, ROSI) and partial agonist (for example, DiBP) are extracted from the simulation trajectory and input them into the Discovery Studio as the receptor pharmacophore model of the full agonists and the partial agonists respectively (the pharmacophore characteristics used in the model are H-bond donor, H-bond acceptor, Hydrophobic and Exclusion Sphere). Then, the full agonists and partial agonists are input respectively to obtain the predicted binding energy. Finally, fit the data from the experimental values of EC15 or EC20 and predicted binding energy.

Embodiment 2

Embodiment 1 Experimental Results

The substances used in the present invention are those from the dust in the background room analysed by Mingliang Fang et al in 2015. The activity data of PPARγ and ligand binding affinity data of PPARγ in the present invention are from this research. The results were shown in table 1:

TABLE 1

The substance activity

| Compounds | EC15 (μM) |
| --- | --- |
| TPP | 2.12 |
| TPPi | NA |
| mono-ITP | 3.6 |
| Di-ITP | 3.25 |
| Tri-ITP | 5.7 |
| TBuP | 5.86 |
| 2,4,6-TIP | 8.72 |
| 2,4,6-TBP | 5.89 |
| TCBPA | 0.23 |
| TBBPA | 0.32 |
| TBPP | NA |
| TBOEP | NA |
| TBBA | 8.16 |
| BDE47 | 5.2 |
| 3-OH-BDE47 | 2.01 |
| 6-OH-BDE47 | NA |
| TCS | NA |
| DiBP | 4.47 |
| DBP | 6.73 |
| BzBP | 2.94 |
| TBMEHP | 0.53 |
| MEHP | 1.26 |
| 15d-PJG2 | 0.51 |
| rosiglitazone (positive control) | 0.00132 |

NA: non-available

The H12 Conformation of PPARγ and Activity Differentiation

Figure 2A:
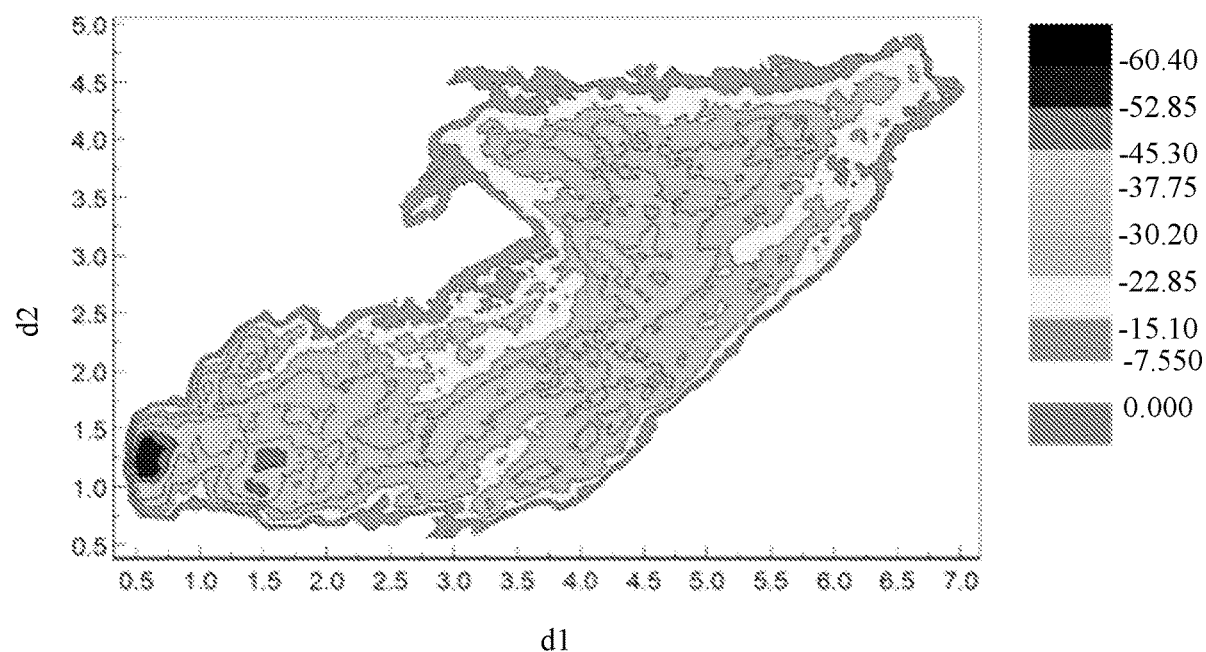
Figure 2B:
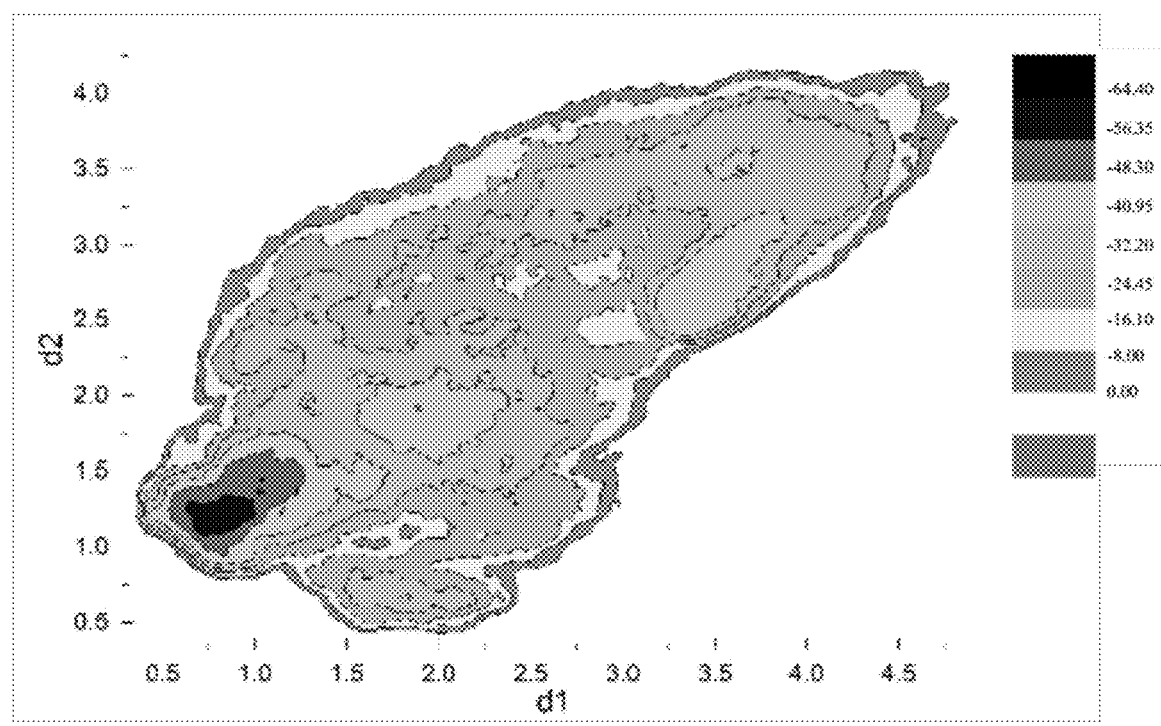
Figure 2C:
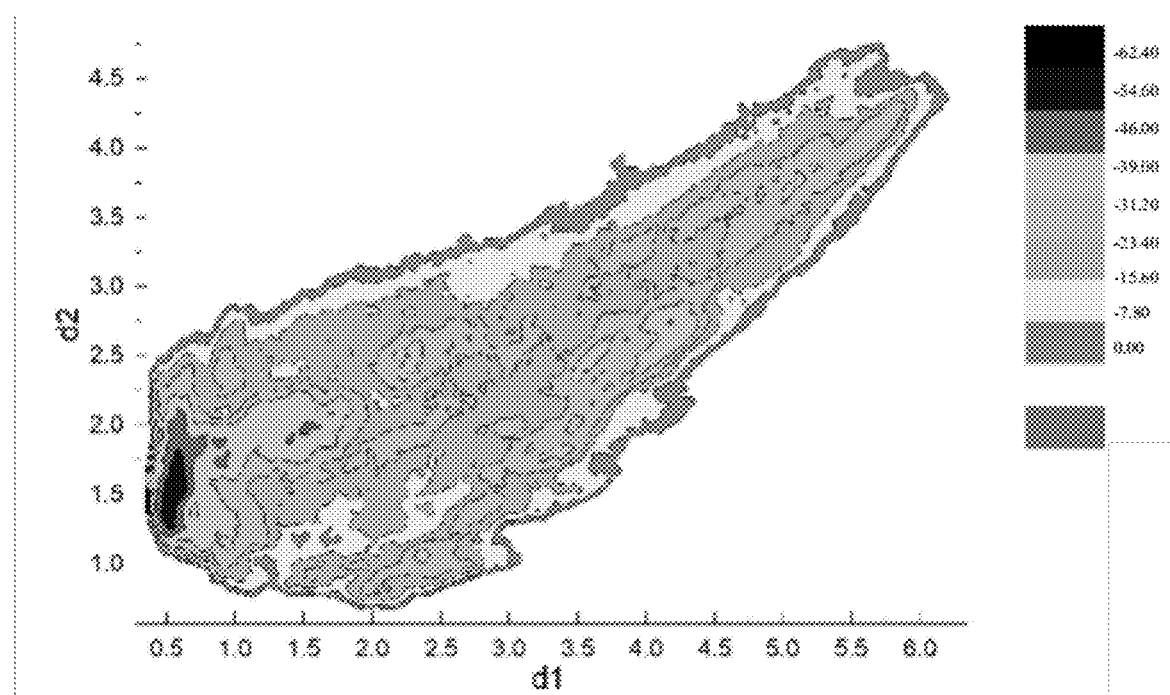
Figure 2D:
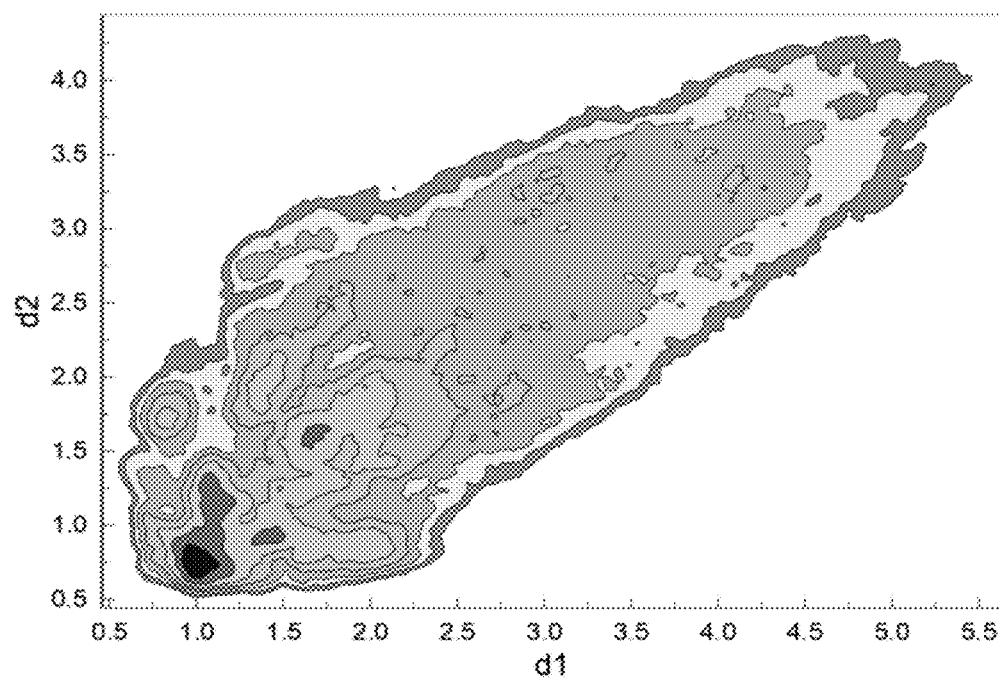
Figure 2E:
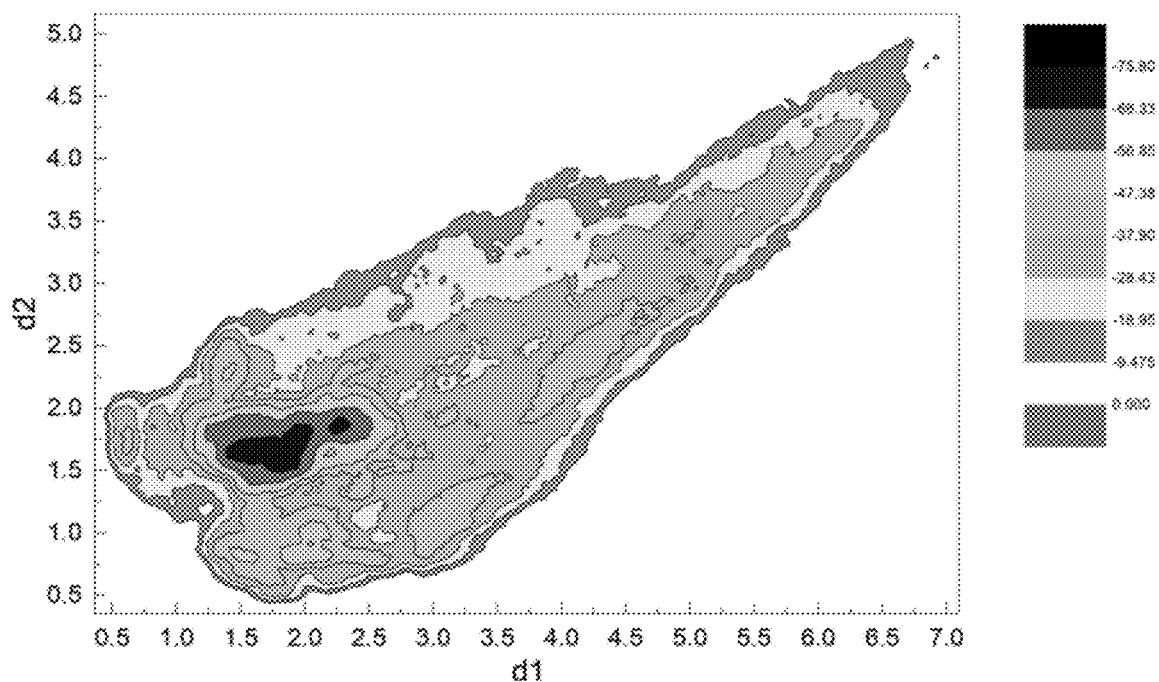
Figure 2F:
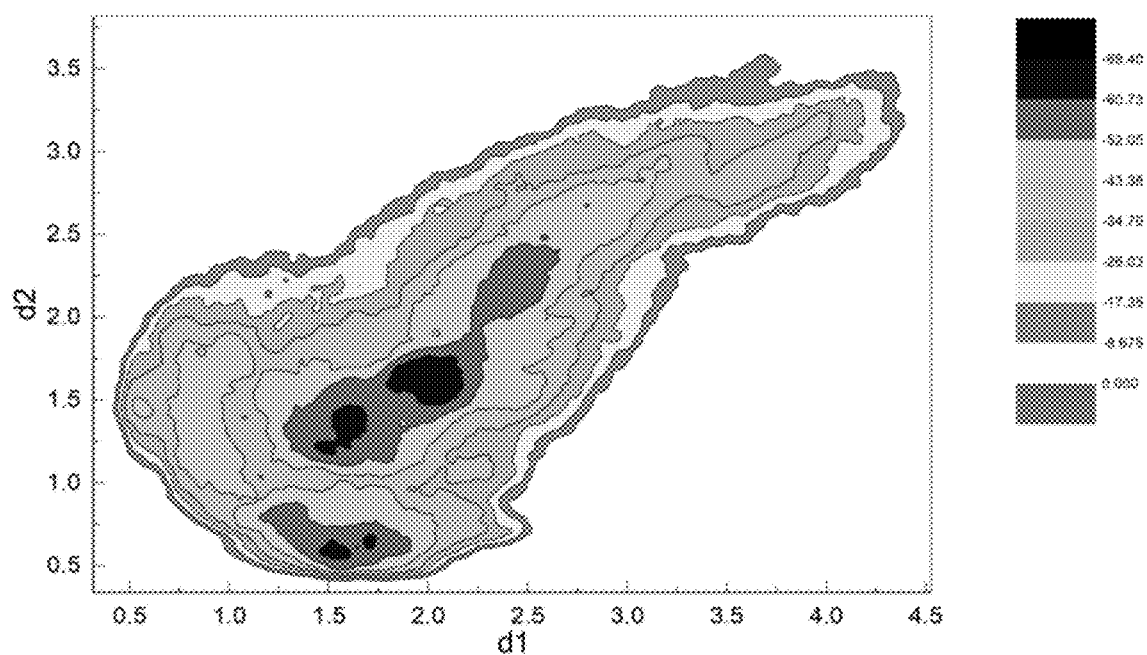
FIG. 2F shows the free energy surface of PPARγ after binding to the antagonists.
Figure 2G:
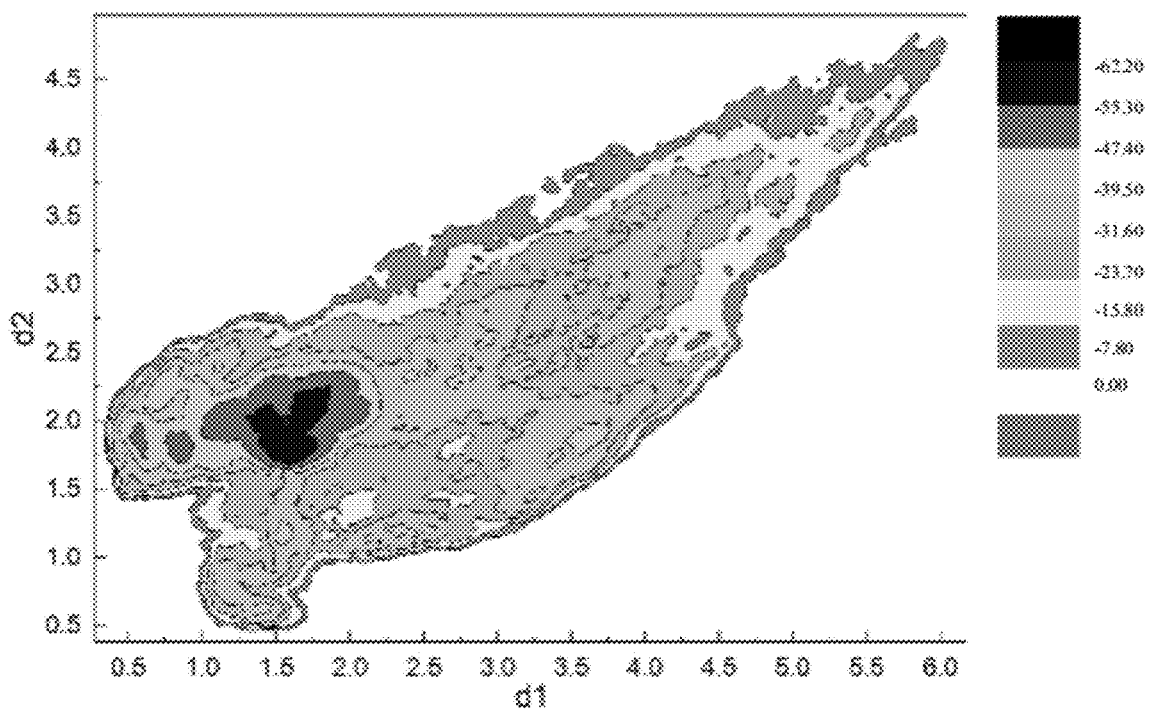
Figure 2H:
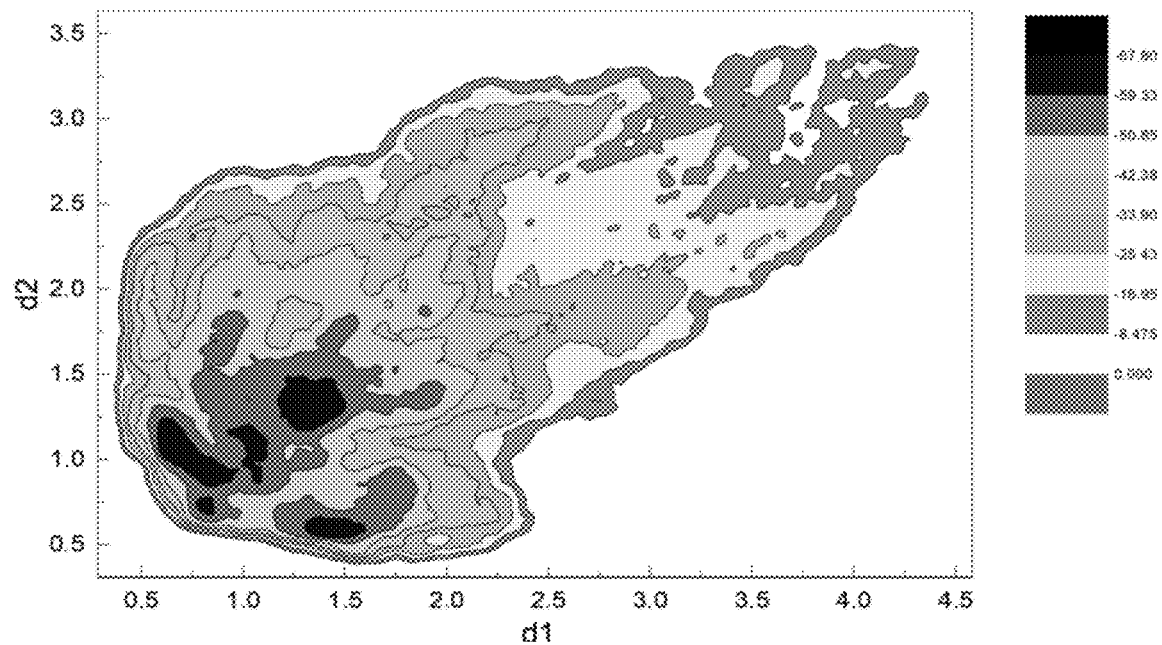
Figure 2I:
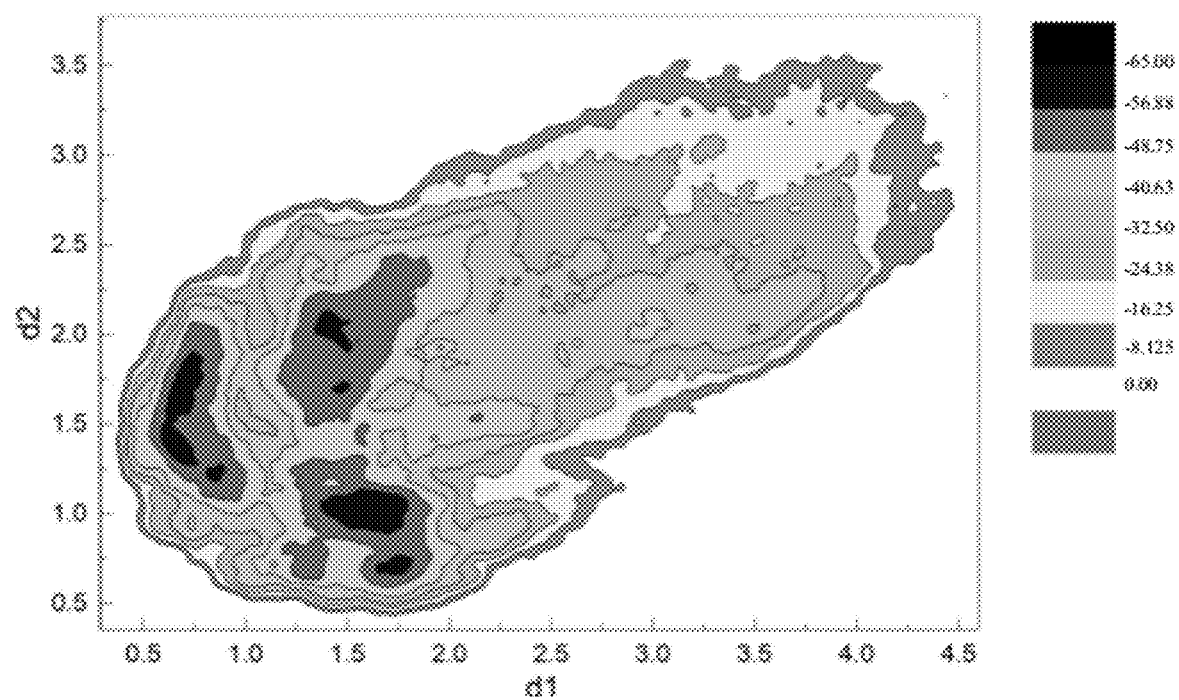
Figure 2J:
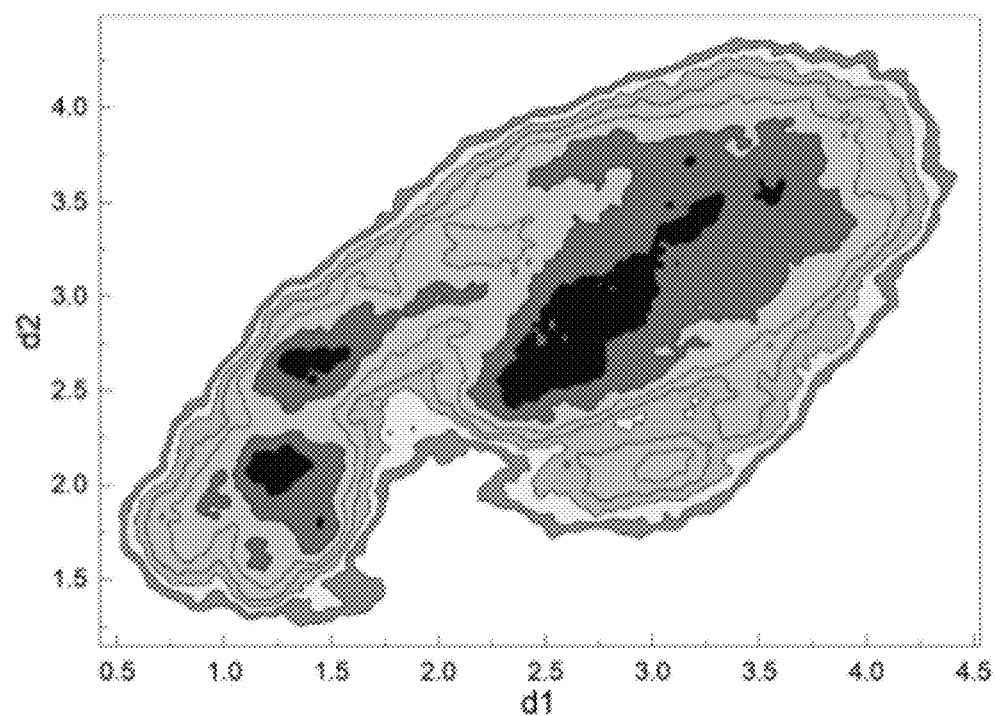
Figure 2K:
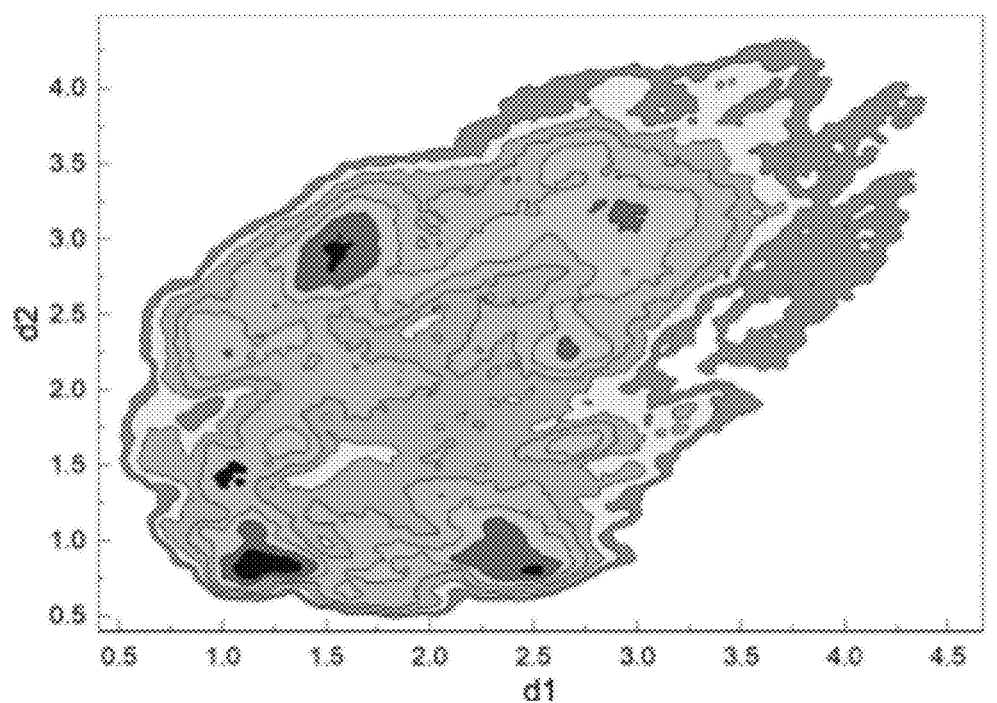
Figure 2L:
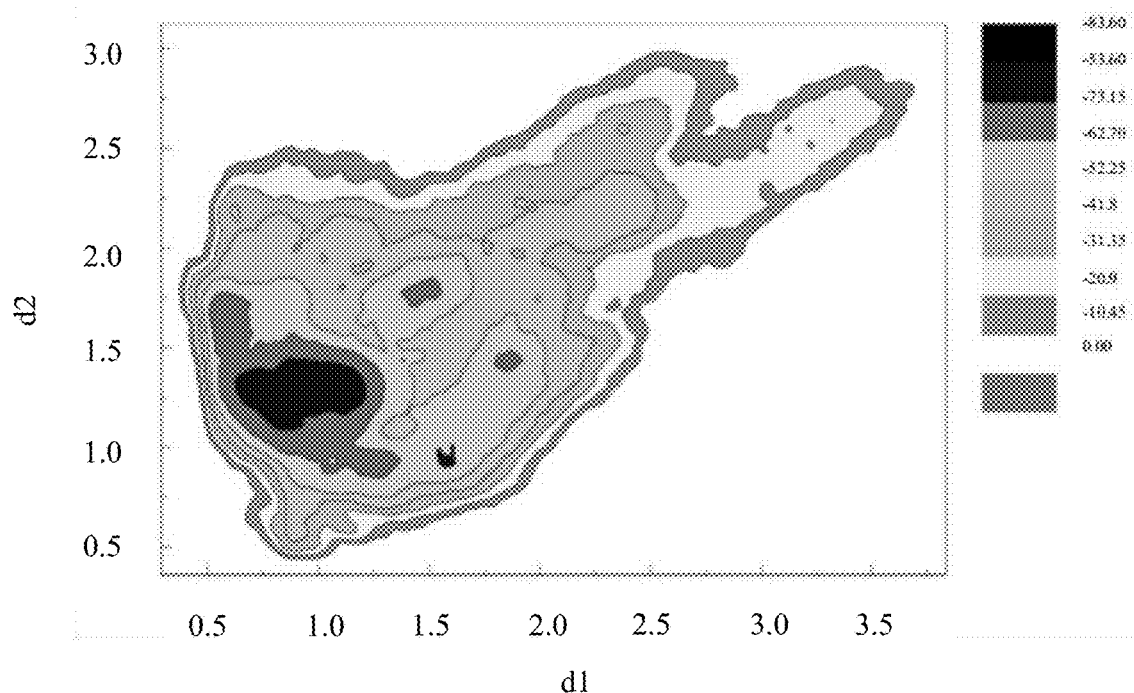
Figure 2O:
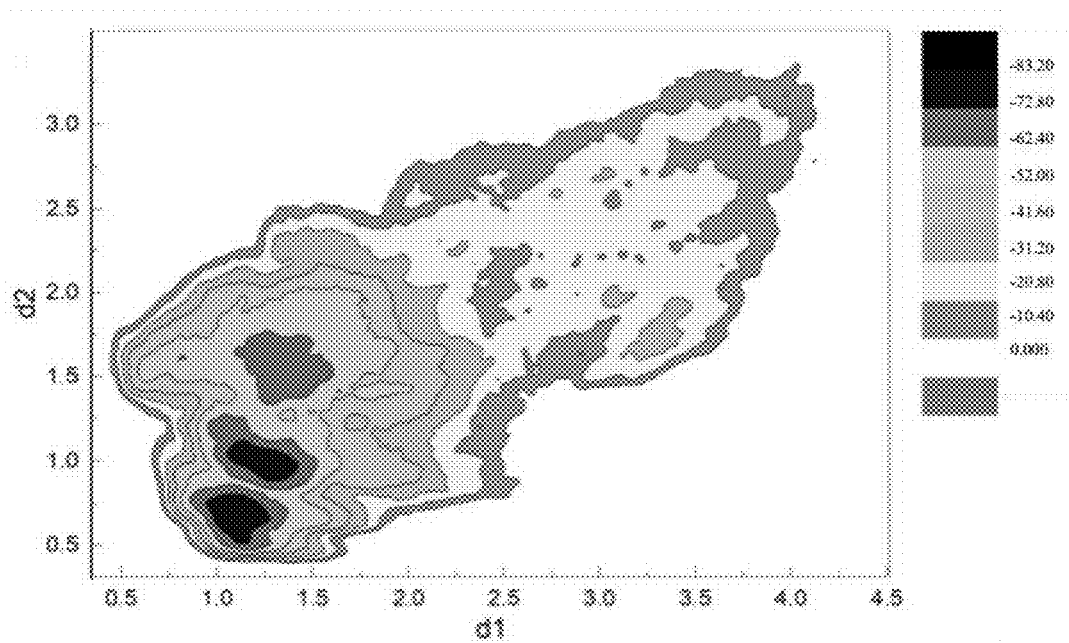
Figure 2M:
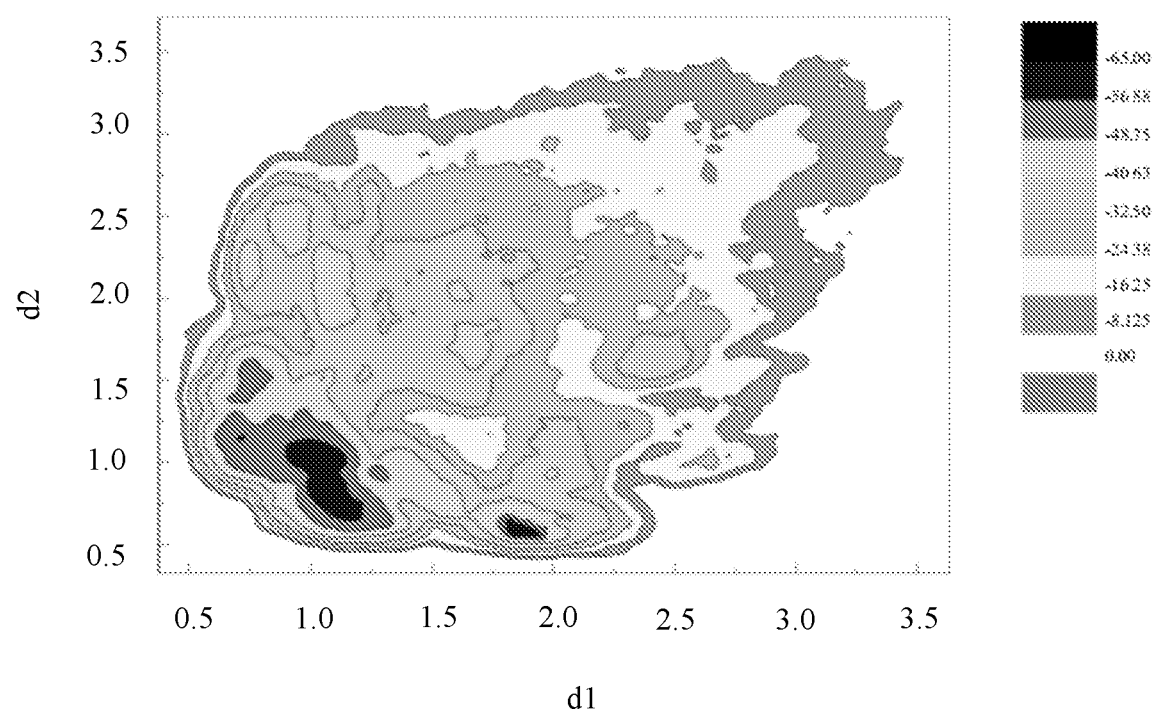
Figure 2N:
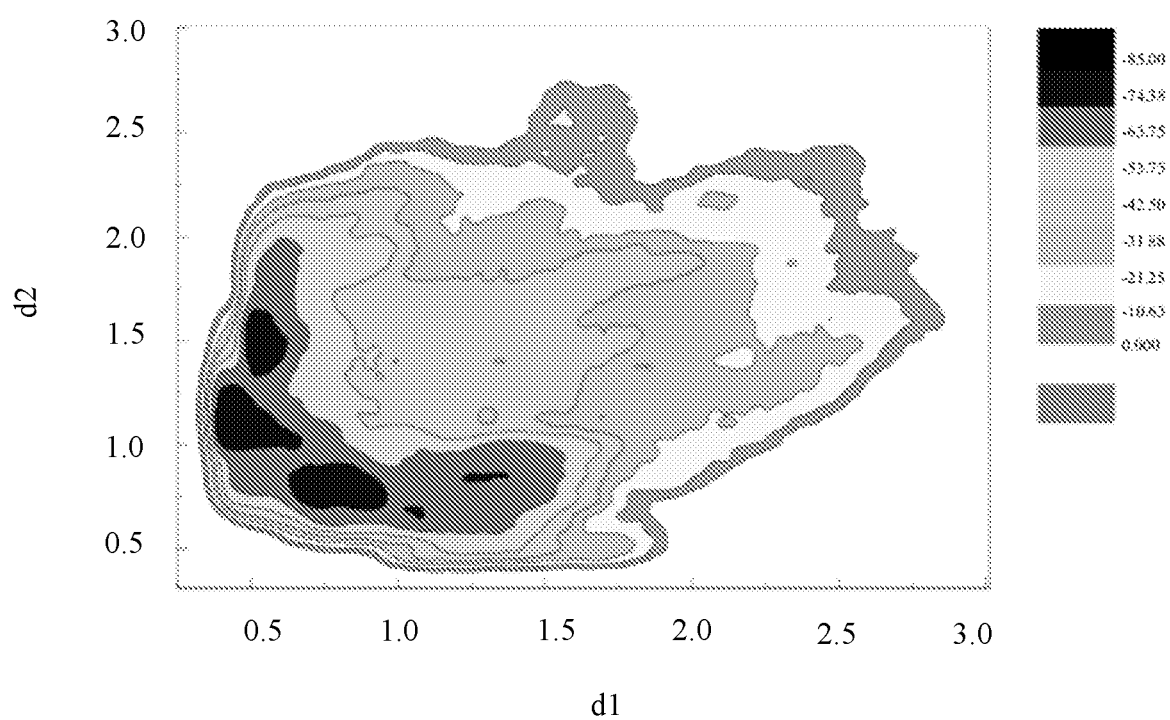
Figure 2P:
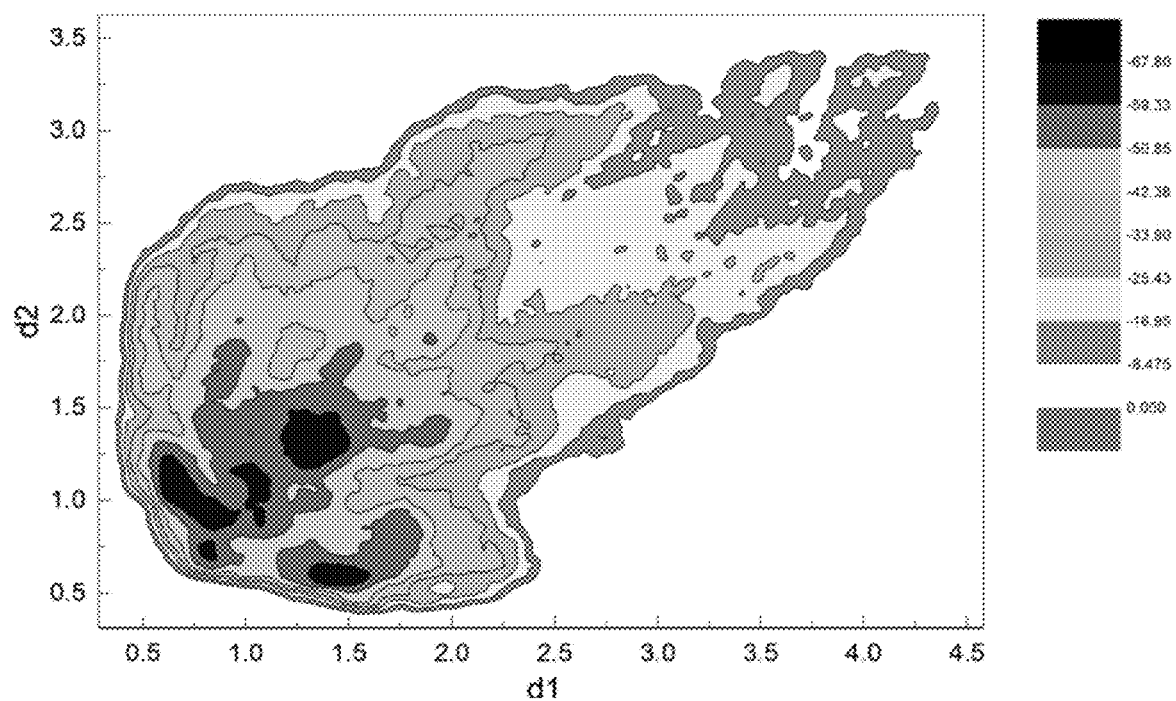
Figure 2Q:
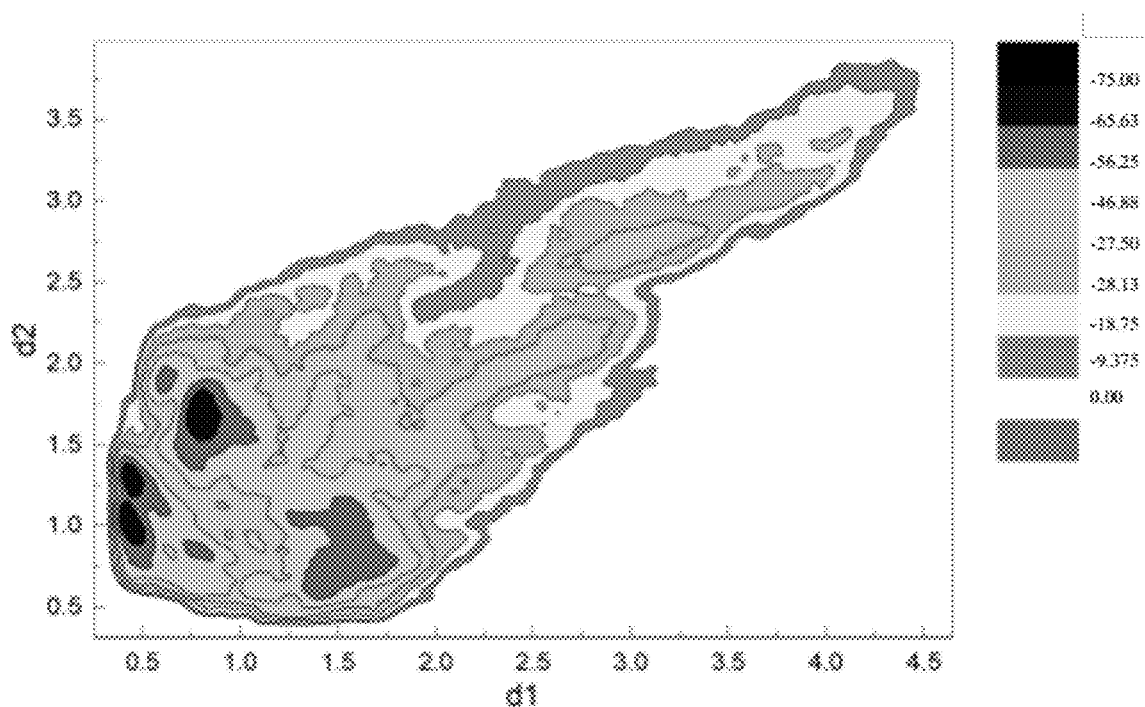
Figure 2R:
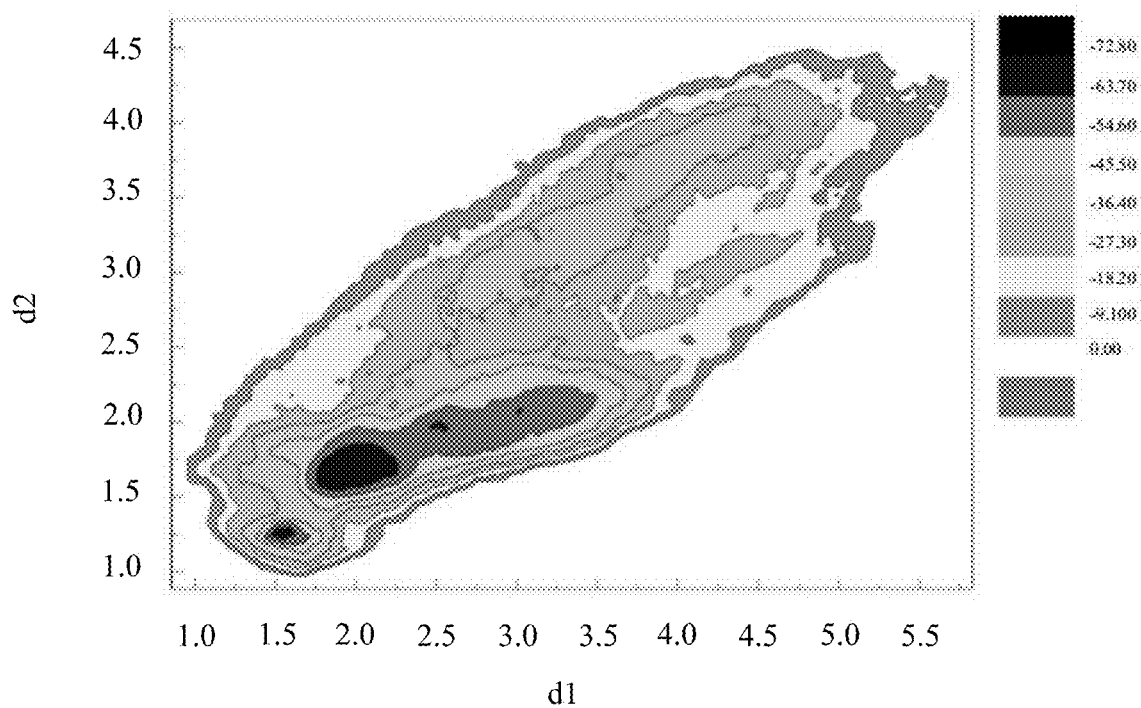
Figure 2T:
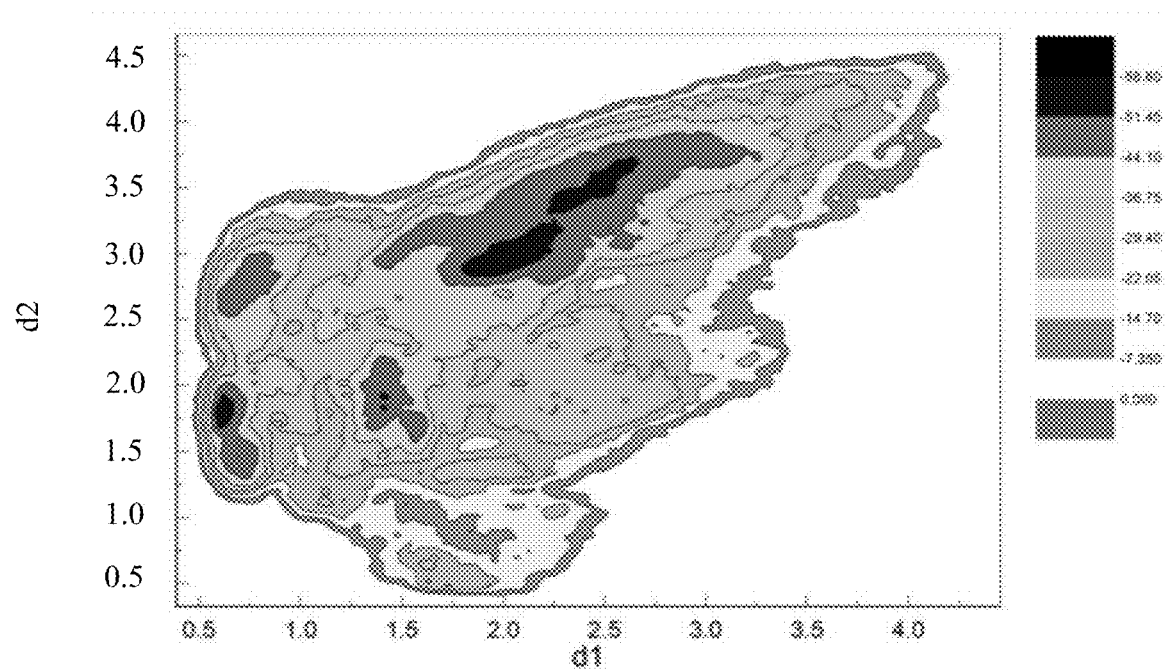
Figure 2S:
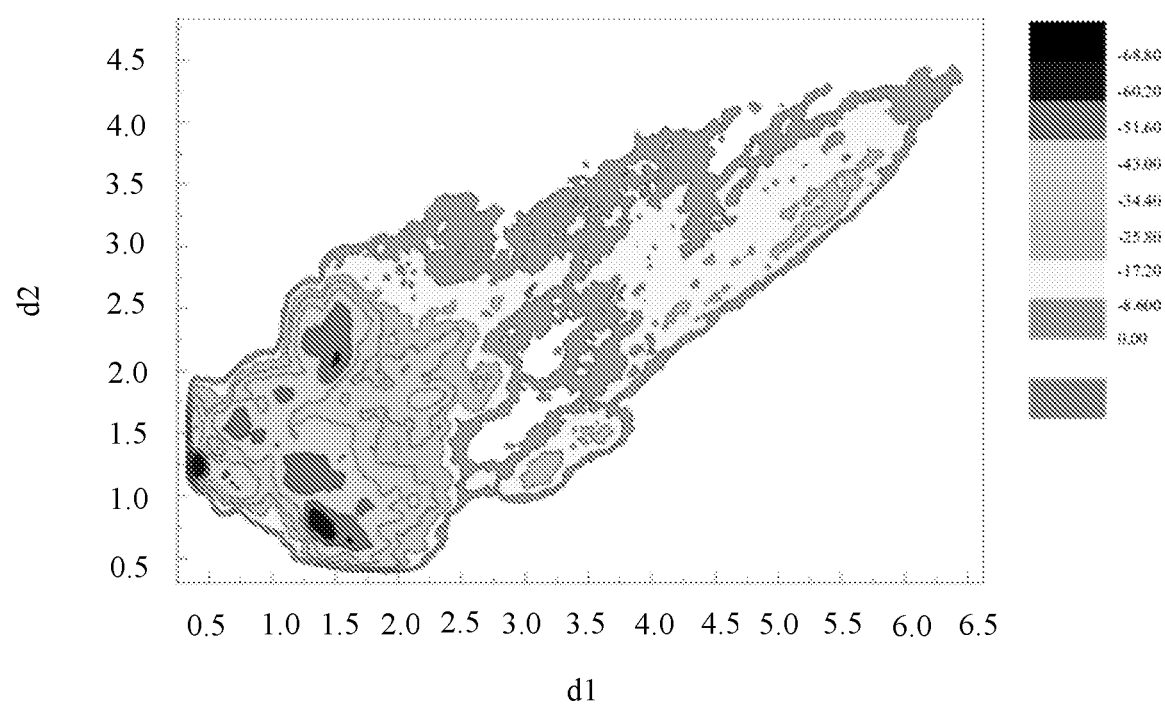
Figure 2U:
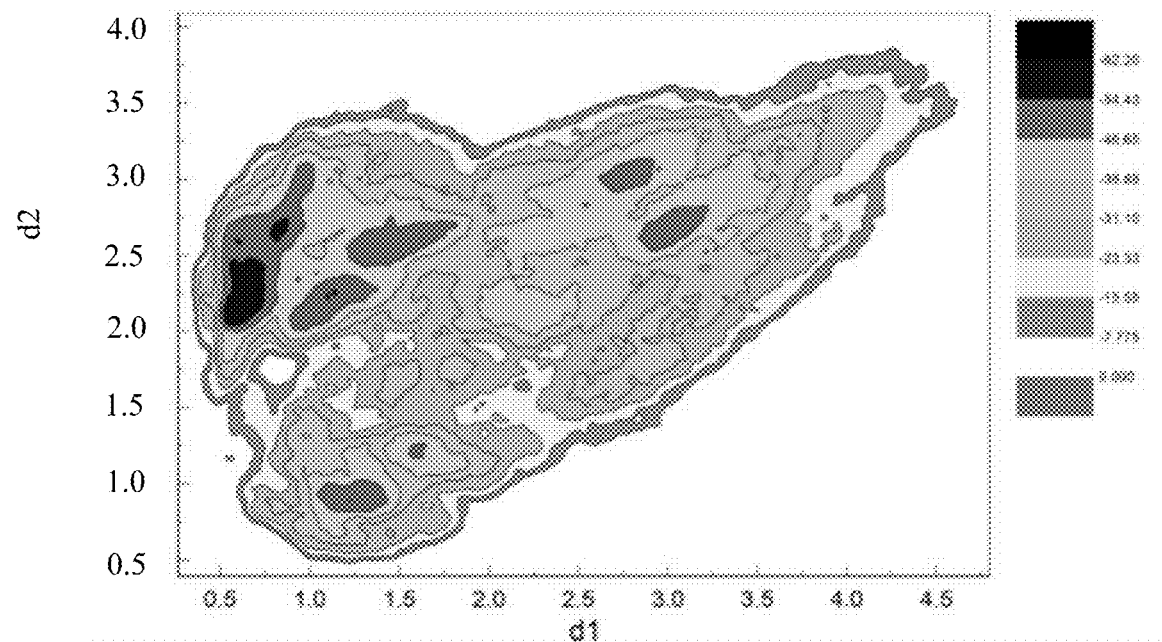
Figure 2X:
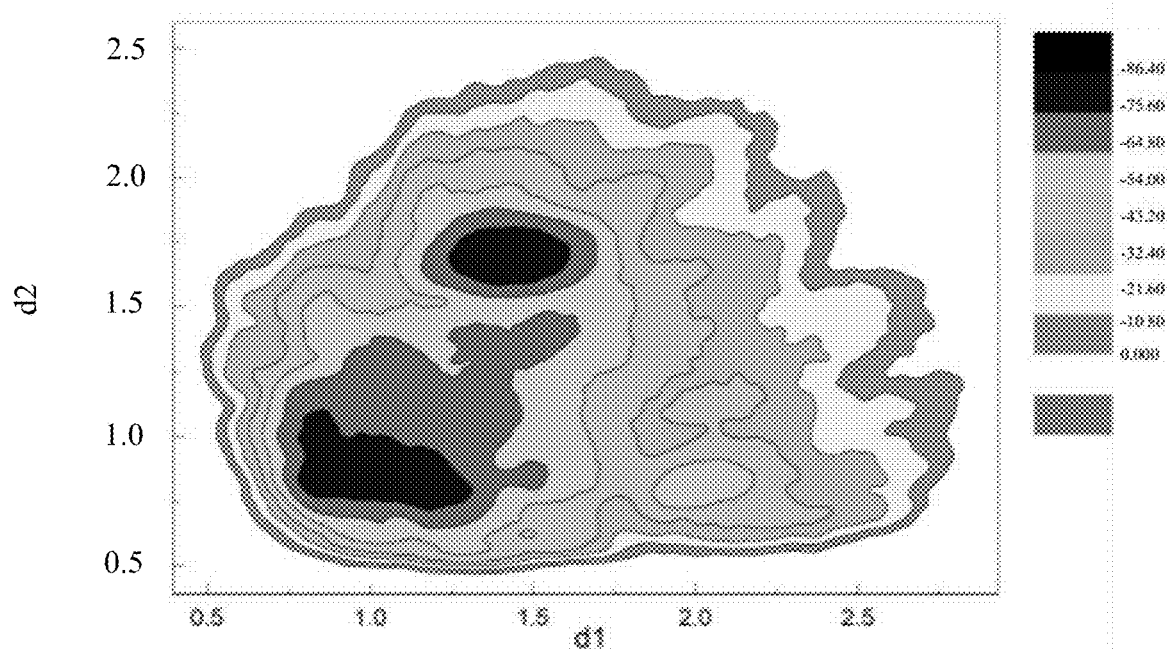
Figure 2V:
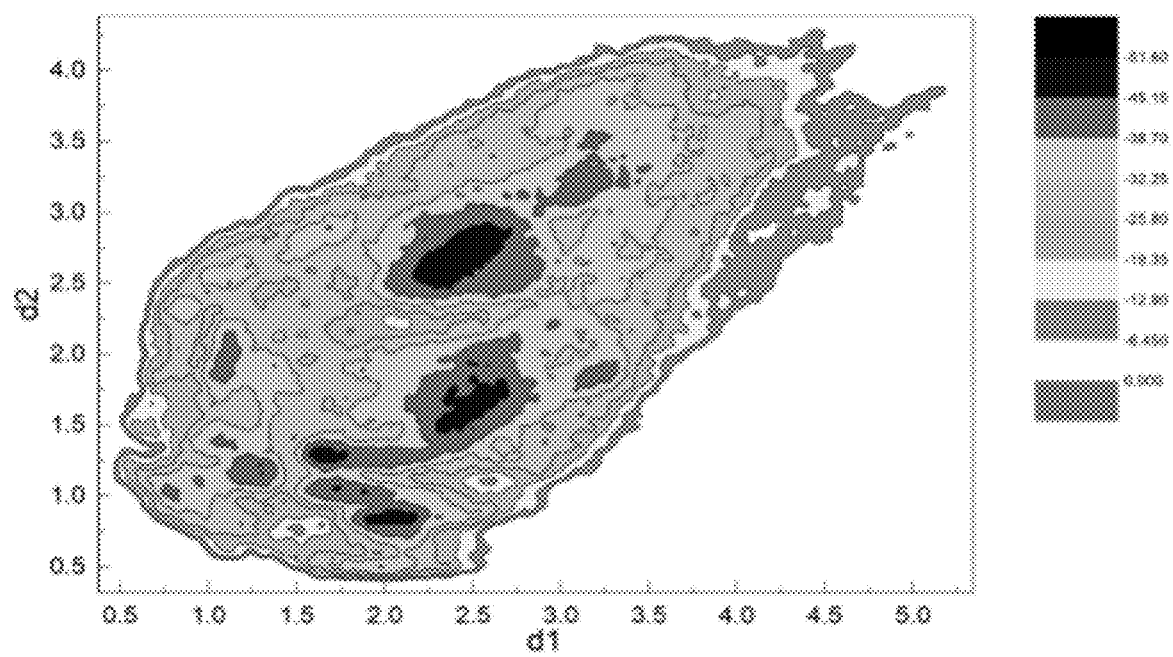
Figure 2W:
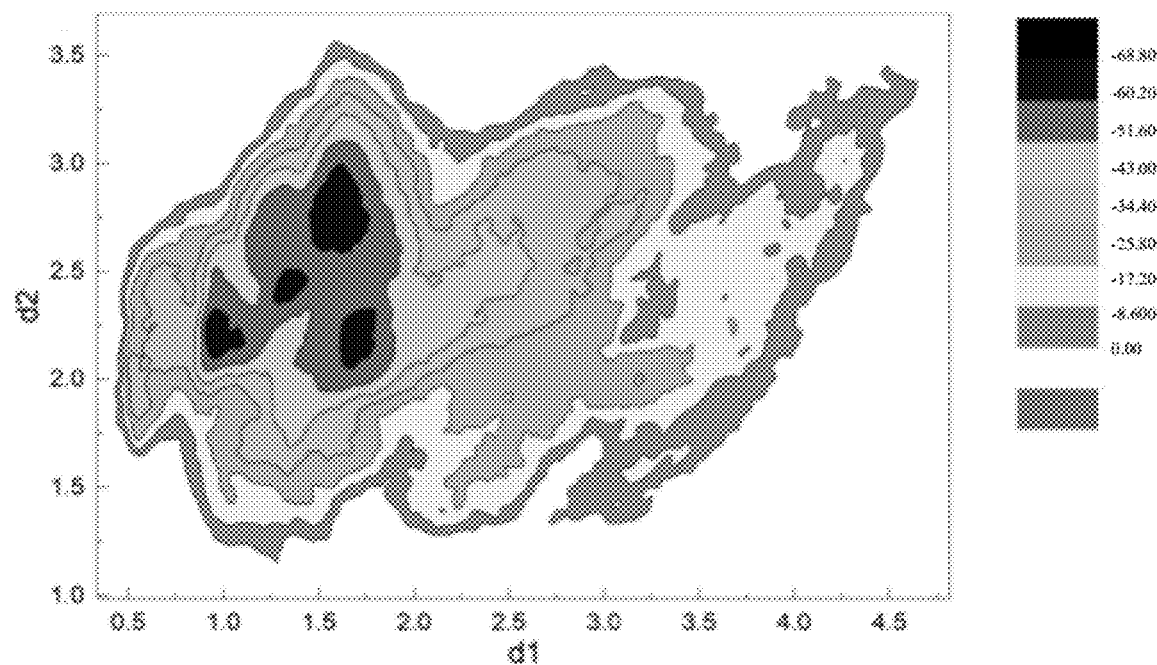
Figure 2Y:
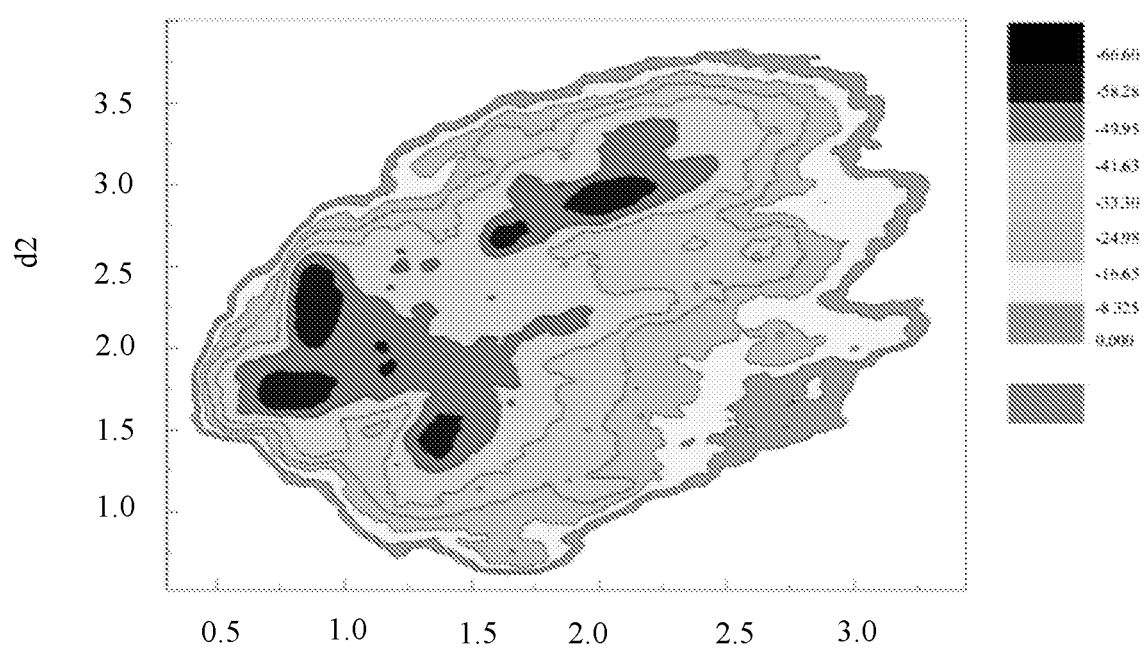
Figure 2Z:
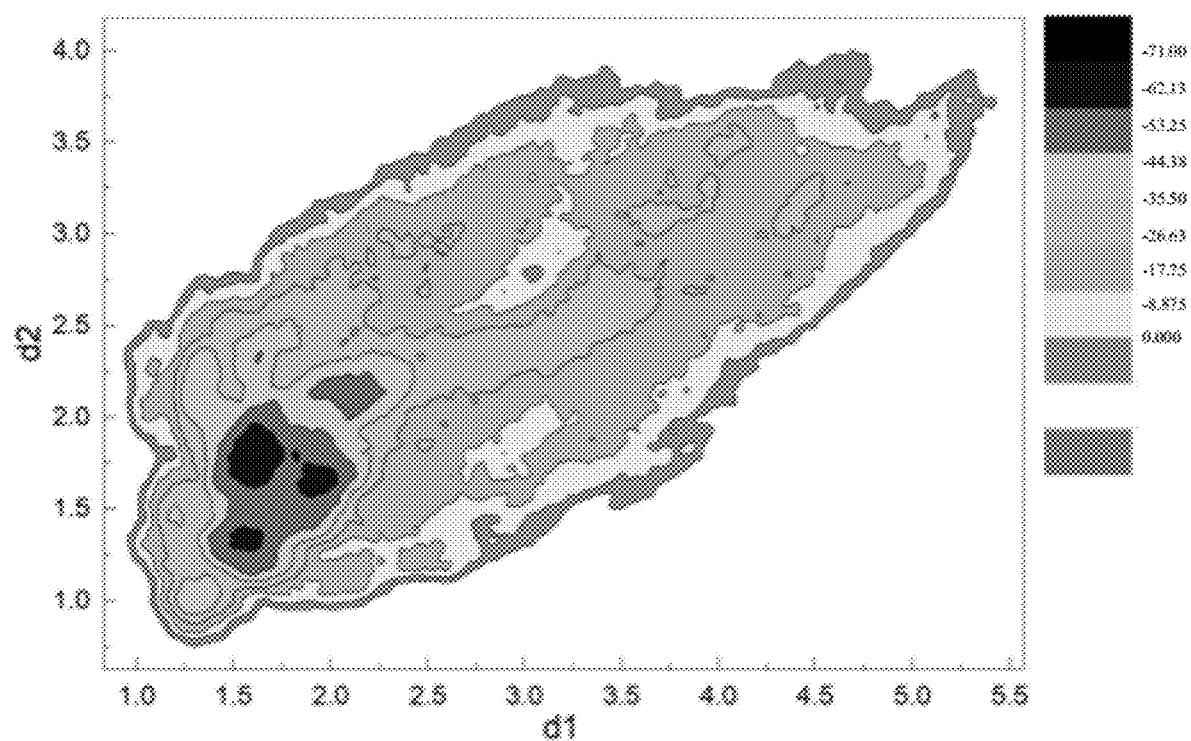
Figure 3A:
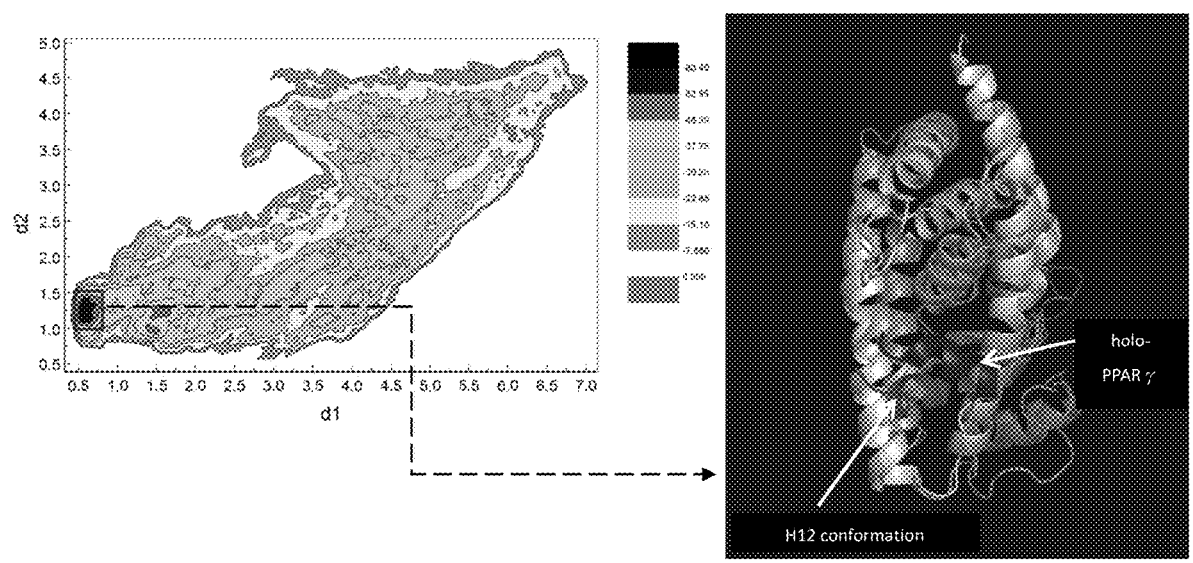

The free energy surfaces of the full agonists, the partial agonists and the antagonists from the WT-metadynamic simulation are shown in FIG. 2A to FIG. 2Z. There are obvious differences between these two free energy surfaces. A large low energy area and one minimum energy area were shown in the free energy surface of PPARγ (FIG. 2A) after binding to the full agonist ROSI. The corresponding conformation of this area is shown in FIG. 3A, and after performing the superposition and comparing to the holo-PPARγ, it is found there is only slightly different between the simulated conformation of PPARγ H12 binding to the agonist ROSI and the holo-PPARγ, which indicates the activated conformation is the only possible conformation after the binding to the agonist.

Figure 3B:
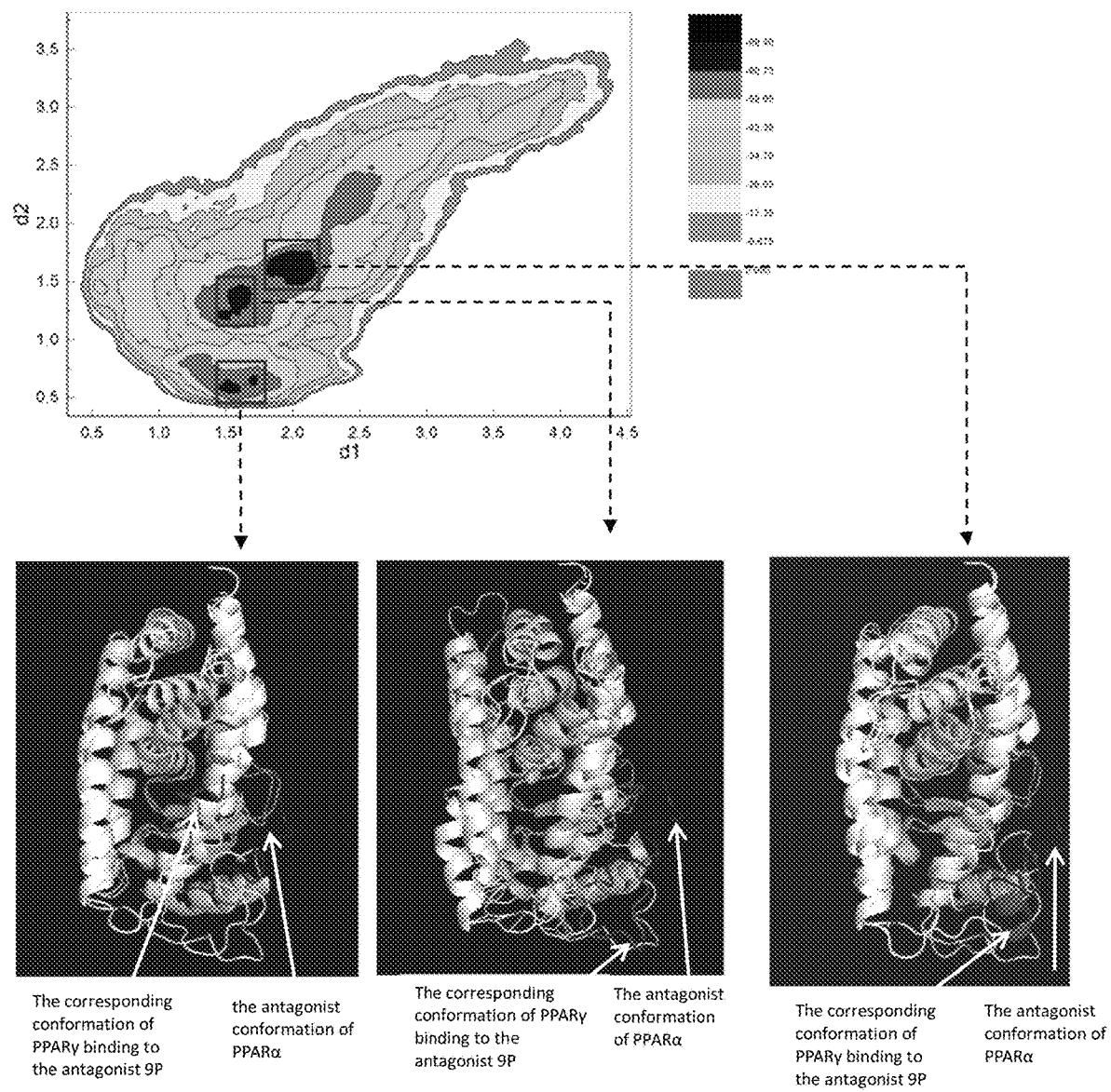

After binding to the antagonists, there are more low energy area of PPARγ and a multiple minimum energy area shown in the free energy surface (FIG. 2F), which indicates that there is more than one PPARγ conformation, and a number of low energy conformations exist after binding to the antagonists. This result demonstrates why the activated conformation of PPARγ is easy to be resolved, but the crystal structure of the antagonist conformation has not been resolved so far (the antagonist conformation of PPARγ is first resolved in the present invention). Moreover, it is shown that the low free energy area after binding to the agonist is not matched to the low free energy area after binding to the antagonist, which indicates the conformation of PPARγ H12 binding to the antagonist is completely different to the activated conformation. The corresponding conformation of this low energy area is shown in FIG. 3B. When overlapping this conformation to the conformation of the PPARα (PDB ID: 1kkq) binding to the antagonist, it was found that comparing to the activated conformation, the stable structure of H12 PPARγ binding to the antagonist was far away from the binding pocket of the receptor. One of the conformations is similar to the antagonist conformation of PPARα with the disappearance of H12 helix and the cofactor AF-2 binding region is occupied, leading to the antagonist effect of PPARγ.

As for the conformation of PPARγ binding to the partial agonist, for example, DiBP (its maximum effect is only 25% of the maximum effect of ROSI) (FIG. 3C) also has multiple low free energy area (FIG. 2P). Compared to the full agonist/antagonist profiles (FIG. 2A or 3A; FIG. 2F or 3B) it is found there are similarities between these low free energy areas. For example, the low free energy area produced by binding the full agonist ROSI also exists in the free energy surface of DiBP, and the low free energy area produced by binding the antagonist 9P also exists in the free energy surface produced by binding to the DiBP. By analysing the corresponding conformation in the corresponding low free energy area, it can be found that there are many stable low energy structures of PPARγ after binding to the DiBP: one of them is similar to the holo-PPARγ, and the other is similar to the antagonist conformation of PPARα. This shows that while binding to the partial agonists, the activated and antagonistic conformations can be generated at the same time, and the energy barrier between these two conformations is relatively low, which is easy to transform to each other. Therefore, binding to the partial agonist is not able to perform stronger activation as binding to the full agonist. The classification of interferences is shown in table 2.

TABLE 2

| Full agonist | Partial agonist | Antagonist |
| --- | --- | --- |
| ROSI, 15d-PJG2, MEHP, TCBPA, BPDP | TBMEHP, 3-OH-BDE47, 6-OH-BDE47, BDE47, TBuP, 2,4,6-TBP, 2,4,6-TIP, BEHF, DBP, DiBP, di- ITP, tri-FTP, mono-ITP, TBBA, TBBPA, TBOEP, TBPP, TCS, TPP, TPPi | 9P |

Figure 3C:
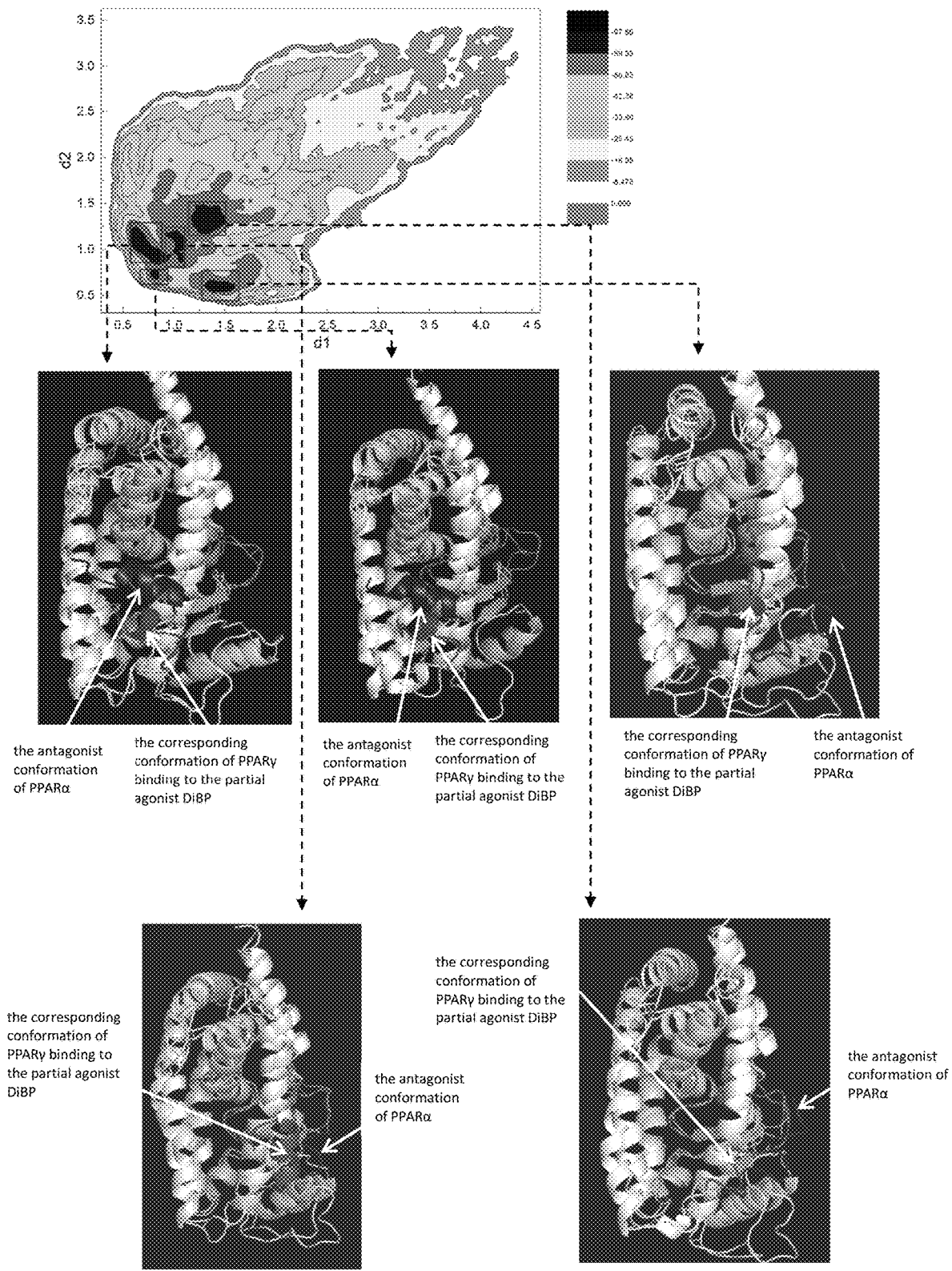

FIG. 2A to FIG. 2Z show the free energy surfaces of conformations of PPARγ H12 binding to different ligands, among which, FIG. 2A to 2E are PPARγ binding to the full agonists ROSI, 15d-PJG2, MEHP, TCBPA, BPDP, respectively; FIG. 2F shows PPARγ binding to the antagonist 9P; FIG. 2G to 2Z are PPARγ binding to the partial agonist TBMEHP, 3-OH-BDE47, 6-OH-BDE47, BDE47, TBuP, 2,4,6-TBP, 2,4,6-TIP, BEHF, DBP, DiBP, di-ITP, tri-ITP, mono-ITP, TBBA, TBBPA, TBOEP, TBPP, TCS, TPP, TPPi, respectively; FIG. 3A to FIG. 3C show the corresponding conformation of the PPARγ H12 binding to the full agonist ROSI of the free energy surfaces and the conformation of holo-PPARγ (FIG. 3A); FIG. 3B shows the corresponding conformation of PPARγ binding to the antagonist 9P and the antagonist conformation of PPARα; FIG. 3C shows the corresponding conformation of PPARγ binding to the partial agonist DiBP and the antagonist conformation of PPARα.

Quantitative Prediction

Figure 4A:
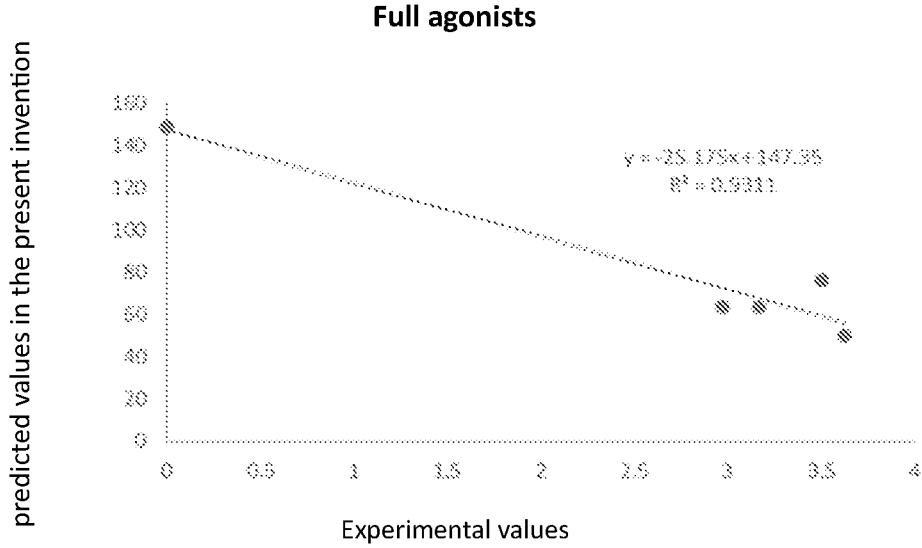
FIG. 4A to FIG. 4B are the correlation diagram between the experimental values and predicted values in the present invention.
Figure 4B:
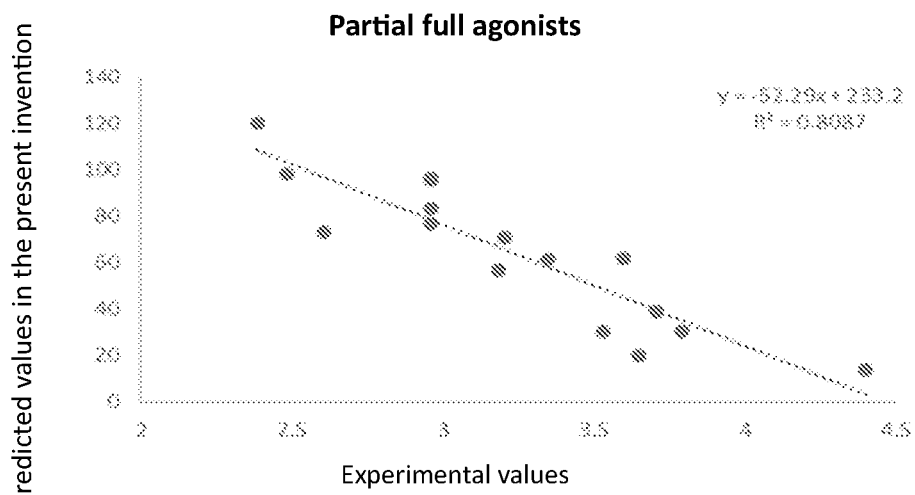

According to the above methods, the ligands were divided into the full agonists, the partial agonists and the antagonists, and the pharmacophore characteristics generated by ROSI and DiBP were used to perform prediction. FIG. 4A to FIG. 4B demonstrate the correlation between the experimental data and the prediction data by the method in the present invention (FIG. 4A is for full agonists and FIG. 4B is for partial agonists). As shown in FIGS. 4A and 4B, the predicted values by the method in the present invention fit well to the experimental values. The $R^2$ of the full agonists was 0.93, and 0.81 for the partial agonists.

Emax is usually used to distinguish the full agonist and the partial agonist of PPARγ, but there is no universal standard. Some researcher uses 60% Emax as the threshold to divide the full agonist and the partial agonist. In the present invention, those selected substances are divided according to the free energy surfaces. It is found that some substances with lower maximal activity, such as TCBPA, belong to the full agonist. Although the binding energy of these substances to PPARγ is low, they would still activate after binding and belong to the full agonist. However, the partial agonists cannot activate the receptor completely after binding to the receptor. According to the free energy surface, the activated and antagonistic conformations exist at the same time.

TABLE 3 the experimental values of the PPARγ binding energy and predicted values for each substance

| Compound | EC15 (μM) | Predicted binding energy (KJ/mol) |
|---|---|---|
| TPP | 2.12 | 70.52 |
| mono-ITP | 3.6 | 83.15 |
| Di-ITP | 3.25 | 95.72 |
| Tri-ITP | 5.7 | 96.30 |
| TBuP | 5.86 | 19.66 |
| 2,4,6-TIP | 8.72 | 3.82 |
| 2,4,6-TBP | 5.89 | 3.65 |
| TCBPA | 0.23 | 63.56 |
| TBBPA | 0.32 | 120.30 |
| TBBA | 8.16 | 30.42 |
| BDE47 | 5.2 | 61.87 |
| 3-OH-BDE47 | 2.01 | 56.89 |
| DiBP | 4.47 | 30.31 |
| DBP | 6.73 | 38.84 |
| BzBP | 2.94 | 61.18 |
| TBMEHP | 0.53 | 73.27 |
| MEHP | 1.26 | 50.18 |
| 15d-PJG2 | 0.51 | 63.64 |
| rosiglitazone (positive control) | 0.00132 | 148.86 |

The present invention firstly uses the molecular dynamics method to simulate and study the conformation changes of PPAR after binding to the full agonist, the antagonist, and the partial agonist, and finds it is still difficult to distinguish the full agonist and the partial agonist, which shows the molecular dynamics simulation is limited by its sampling efficiency and cannot have the low energy conformation of PPARγ after binding to the partial agonist. After using Well-Tempered Meta-dynamics molecular dynamics simulation, the present invention obtains the free energy surfaces of PPARγ after binding to the full agonist, the partial agonist and the antagonist. The present invention can qualitatively distinguish PPARγ activity through free energy surfaces, wherein PPARγ only has activated conformation after binding to the full agonists and has activated conformation and antagonist conformation at the same time after binding to the partial agonists. The present invention can quickly distinguish PPARγ activity of different structural compounds and greatly reduce the use of chemicals and cells in the laboratory in the process of traditional toxicological experiment, the workload of the laboratory and save the expenses of the laboratory; Therefore, PPARγ activity of compounds is distinguished before QSAR modeling, which makes the results of QSAR modeling close to the reality, such that the conventional QSAR can be widely used.

It should be noted that the above embodiments are only used to explain the technical scheme of the invention, not the limitation. Although the invention is described in detail with reference to the preferred embodiments, it should be understood by those skilled in the art that the technical scheme of the invention can be modified or replaced equally without departing from the spirit and scope of the technical scheme of the invention which should be covered in the right of the invention.

The invention claimed is:

1. A method of identifying endocrine disrupting chemicals by determining whether a molecule of interest is a peroxisome proliferator-activated receptor γ full agonist, partial agonist or antagonist by analyzing a binding energy, the method comprising:

providing a simulated protein receptor mimicking said peroxisome proliferator-activated receptor γ and a simulation of the molecule of interest;

docking the simulation of the molecule of interest and the simulated protein receptor to form a docked conformation;

performing at least two rounds of molecular dynamic simulation to obtain at least one trajectory and at least one free energy surface, wherein one of the at least two rounds of molecular dynamic simulation comprises adopting a collective variable (CV) 1 and a CV2, wherein the CV1 is a first distance between Cα of Tyr473 on H12 and Cα of Leu453 on H11 of the peroxisome proliferator-activated receptor γ, and CV2 is a second distance between Cα of Tyr473 on H12 and Cα of Lys319 on H4 of the peroxisome proliferator-activated receptor γ;

inputting the trajectory to construct at least one pharmacophore and obtaining a binding energy diagram of the simulation of the molecule of interest docked on the simulated protein receptor; and analyzing the binding energy diagram of simulation of the molecule of interest docked on the simulated protein in order to determine whether the molecule of interest is the peroxisome proliferator-activated receptor γ full agonist, partial agonist or antagonist;

wherein if the molecule of interest is a full agonist, the binding energy diagram shows one low energy area; and if the molecule of interest is an antagonist or a partial agonist, the binding energy diagram shows multiple low energy areas.

2. The method of claim 1, wherein said providing the simulated protein receptor comprises removing at least one small molecule mekt21 in a A chain and a B chain from said simulated protein receptor; removing at least one water molecule to form a remaining B chain protein, wherein the remaining B chain protein after removal of the at least one small molecule mekt21 and the at least one water molecule is saved as a template for a homology modeling prior to said performing at least two rounds of simulation.

3. The method of claim 1, wherein said docking simulation of the molecule of interest and the simulated protein receptor to form the docked conformation comprises searching a binding pocket with a threshold value of 0.5 and a bloat value of 0.

* * * * *